United States Patent
Wehrli

[11] Patent Number: 5,849,917
[45] Date of Patent: Dec. 15, 1998

[54] PROCESS FOR THE PREPARATION OF ISOQUINOLINE COMPOUNDS

[75] Inventor: Christof Wehrli, Witterswil, Switzerland

[73] Assignee: Roche Vitamins Inc., Parsippany, N.J.

[21] Appl. No.: 924,625

[22] Filed: Sep. 5, 1997

[30] Foreign Application Priority Data

Oct. 2, 1996 [EP] European Pat. Off. ............ 96115782

[51] Int. Cl.$^6$ ................................................. C07D 217/16
[52] U.S. Cl. ........................................................... 546/146
[58] Field of Search ............................................. 546/146

[56] References Cited

U.S. PATENT DOCUMENTS

| | | | |
|---|---|---|---|
| 3,810,899 | 5/1974 | Mohacsi et al. | 546/146 |
| 3,914,232 | 10/1975 | Mohacsi et al. | 546/146 |
| 3,914,233 | 10/1975 | Mohacsi et al. | 546/146 |
| 3,914,234 | 10/1975 | Mohacsi et al. | 546/146 |
| 4,857,648 | 8/1989 | Broger et al. | 546/146 |
| 5,360,908 | 11/1994 | Broger et al. | 546/146 |

FOREIGN PATENT DOCUMENTS 2 311 881   9/1973   Germany .

OTHER PUBLICATIONS

Kitamura et al., "General Asymetric Synthesis of Benzomorphans and Morphinans via Enantioselective Hydrogenation", Tetrahedron Letters, vol. 28, No. 41, pp. 4829–4832 (1987).
Kitamura et al., "General Asymetric Synthesis of Isoquinoline Alkaloids", J. Org. Chem. 59:297–310 (1994).
Schnider et al., "Synthesis of Morphinan", Helv. Chim. Acta, 33:1437–1448 (1950).
Walter et al., "Synthesis in the Class of Isoquinoline 1,2, substitute Octahydroisoquinoline", Helv. Chim. Acta, 44:1546–1554 (1961).

Primary Examiner—Zinna Northington Davis
Attorney, Agent, or Firm—George W. Johnston; Dennis P. Tramaloni; Bruce A. Pokras

[57] ABSTRACT

(Z)-1[1-(4-Methoxybenzylidene)-1,2,3,4,5,6,7,8-octahydroisoquinolin-2-yl]alkanones of the formula

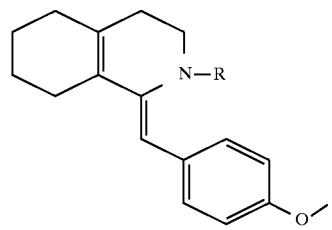

I wherein R is lower alkanoyl, can be produced under specific reaction conditions in a one-pot process in an advantageous manner by a Bischler-Napieralski cyclization of N-(2-cyclohex-1-enylethyl)-2-(4-methoxyphenyl)-acetamide and subsequent lower-alkanoylation of the resulting 1-(4-methoxybenzyl)-3,4,5,6,7,8-hexahydro-isoquinoline of the formula

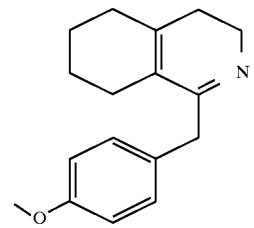

III under an inert gas atmosphere and, if desired converted to dextomethorphan in a known manner.

16 Claims, No Drawings

PROCESS FOR THE PREPARATION OF ISOQUINOLINE COMPOUNDS

BACKGROUND OF THE INVENTION

Field of the Invention

The present invention relates to a process for making (Z)-1[1-(4-methoxybenzylidene)-1,2,3,4,5,6,7,8-octahydro-isoquinolin-2-yl]alkanones.

SUMMARY OF THE INVENTION

The present invention relates to a process for preparing a compound of the formula

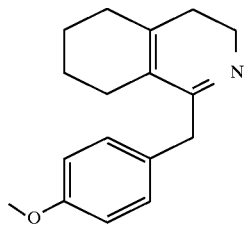

wherein R is lower alkanoyl;
by Bischler-Napieralski cyclization of the compound of the formula

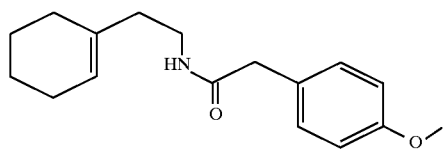

in the presence of 0.45 to 0.8 mol equivalents of phosphorous oxychloride and subsequent in situ alkanoylation of the compound of the formula

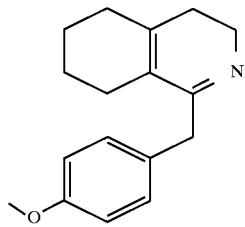

in the presence of a weak organic base which is inert under the reaction conditions.

DETAILED DESCRIPTION OF THE INVENTION

The present invention relates to a process for the production of (Z)-1-[1-(4-methoxybenzylidene)-1,2,3,4,5,6,7,8-octahydro-isoquinolin-2-yl]alkanones of the formula

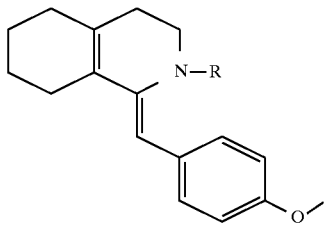

wherein R is lower alkanoyl,
by a Bischler-Napieralski cyclization of N-(2-cyclohex-1-enylethyl)-2-(4-methoxyphenyl)acetamide of the formula

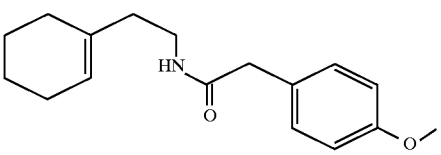

with phosphorus oxychloride and subsequent alkanoylation of the resulting 1-(4-methoxybenzyl)-3,4,5,6,7,8-hexahydro-isoquinoline of the formula

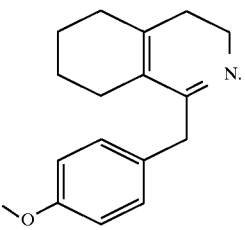

The term "lower alkanoyl" used in this description signifies not only straight-chain, but also branched residues of an aliphatic carboxylic acid with 2 to 7 carbon atoms, such as acetyl, propionyl, butyryl, valeryl and the like, with acetyl being especially preferred.

The (Z)-1-[1-(4-methoxybenzylidene)-1,2,3,4,5,6,7,8-octahydro-isoquinoline-2-yl]alkanones of formula I above are important starting materials for the manufacture of dextromethorphan of the formula

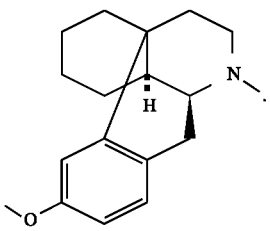

They can be converted into dextromethorphan in a known manner, for example, in analogy to the procedures described in German Offenlegungsschrift 2 311 881 corresponding to U.S. Pat. No. 3,810,899 issued May 14, 1974 by reduction of the exocyclic double bond, cyclization with a strong acid to the corresponding morphinan derivative, cleavage of the residue R and N-methylation. The use of the (Z)-1-[1-(4-methoxybenzylidene)-1,2,3,4,5,6,7,8-octahydro-isoquinolin-2-yl]alkanones for the manufacture of dextromethorphan is also an object of the present invention.

A process for the production of 1-(4-methoxybenzyl)-3,4,5,6,7,8-hexahydro-isoquinoline from N-(2-cyclohex-1-enylethyl)-2-(4-methoxyphenyl)acetamide is described in Helv. Chim. Acta 33, 1437 (1950). According to this known process, the N-(2-cyclohex-1-enylethyl)-2-(4-methoxyphenyl)acetamide of formula II above is cyclized with an excess of phosphorus oxychloride and the 1-(4-methoxybenzyl)-3,4,5,6,7,8-hexahydro-isoquinoline hydrochloride obtained is isolated by extraction in the form of the free base after basifying the reaction mixture. Because the free base 1-(4-methoxybenzyl)-3,4,5,6,7,8-hexahydro-isoquinoline is not storage-stable, it is therefore of advantage in accordance with Helv. Chim. Acta 44, 1546 (1961) to extract not the free base, but the storage-stable hydrochloride salt with chloroform. The reason for this chloroform extraction is the fact that the isoquinoline salt obtained can be extracted practically only with a chlorinated solvent. Since on the one hand the use of an excess of phosphorus oxychloride is uneconomical and on the other hand the use of an excess of this reagent and of chlorinated solvents without costly waste management is no longer acceptable today for reasons of environmental protection, a process using amounts of phosphorus oxychloride which are as low as possible and without using chlorinated solvents is of great interest from the industrial viewpoint.

The production of (Z)-1-[1-(4-methoxybenzylidene)-1,2,3,4,5,6,7,8-octahydro-isoquinolin-2-yl]ethanone from isolated 1-(4-methoxybenzyl)-3,4,5,6,7,8-hexahydro-isoquinoline in a multi-stage process is also described in U.S. Pat. No. 4,857,648, but the yields achievable with this process are insufficient for an industrial application.

The object of the present invention is accordingly to provide a process for the production of (Z)-1-[1-(4-methoxybenzylidene)-1,2,3,4,5,6,7,8-octahydro-isoquinolin-2-yl]alkanones of formula I by the cyclization of N-(2-cyclohex-1-enylethyl)-2-(4-methoxyphenyl)acetamide and subsequent N-alkanoylation, which does not have the disadvantages of the known procedures (use of excess phosphorus oxychloride, multi-stage synthesis, low yields and use of a chlorinated solvent).

In the scope of the present invention, this object has been achieved by carrying out the two reaction steps without isolation of the intermediate product in a one-pot process under the specific reaction conditions described below in detail.

Accordingly, the present invention is concerned with a process for the production of (Z)-1-[1-(4-methoxybenzylidene)-1,2,3,4,5,6,7,8-octahydro-isoquinolin-2-yl]alkanones of formula I above by a Bischler-Napieralski cyclization of N-(2-cyclohex-1-enylethyl)-2-(4-methoxyphenyl)acetamide of formula II above and subsequent lower-alkanoylation of the resulting 1-(4-methoxybenzyl)-3,4,5,6,7,8-hexahydro-isoquinoline of formula III above under an inert gas atmosphere, which process comprises carrying out the Bischler-Napieralski cyclization in the presence of 0.45 to 0.8 molar equivalents of phosphorus oxychloride, if desired diluting the reaction solution from the Bischler-Napieralski cyclization with an aprotic organic solvent which is inert under the reaction conditions and lower-alkanoylating the resulting 1-(4-methoxybenzyl)-3,4,5,6,7,8-hexahydro-isoquinoline in situ, that is, without isolation, in the presence of a weak organic base which is inert under the reaction conditions.

The Bischler-Napieralski cyclization is carried out in a known manner in an aprotic organic solvent which is inert under the reaction conditions at a temperature between about 70° C. and a temperature which lies just below the reflux temperature of the reaction mixture. Aromatic hydrocarbons, such as toluene or xylene, nitriles, such as propionitrile or butyronitrile, and the like, especially toluene or propionitrile, primarily toluene, have been found to be especially suitable for the purpose of the present invention. The reaction temperature preferably lies between about 80° and 110° C., especially between about 80° and 100° C. At temperatures below 70° C. the Bischler-Napieralski cyclization becomes too slow and at above 110° C. the formation of byproducts increases. Somewhat fewer byproducts are formed when the dilution is increased, but then the yield is not improved. Preferably, 0.5 to 0.55 molar equivalents of phosphorus oxychloride are used. The rate at which the phosphorus oxychloride is added is not critical when the reaction temperature remains constant, although a slow addition improves the yields slightly. In an especially preferred embodiment the phosphorus oxychloride is added continuously at 80° C. and, after completion of the addition, the reaction mixture is heated stepwise or continuously to 100° C.

The reaction step comprising the lower-alkanoylation is also carried out in a known manner at a temperature between about room temperature and 80° C. in the presence of 2–4 molar equivalents (based on phosphorus oxychloride) of a weak organic base which is inert under the reaction conditions under an inert gas atmosphere, preferably under nitrogen or argon, since the presence of even only traces of oxygen exert a very negative effect on the yield. In order to achieve a yield which is as high as possible, an exclusion of oxygen is therefore absolutely necessary. It has accordingly been found to be advantageous to carry out the alkanoylation not only under an inert gas atmosphere, but to use all solvents and reagents in the oxygen-free state. Although the exclusion of oxygen is necessary only for the alkanoylation, for reasons of convenience the preceding cyclization with phosphorus oxychloride is also carried out with the exclusion of oxygen.

The anhydrides and chlorides, preferably the anhydrides, of lower alkanecarboxylic acids can be used as alkanoylating agents, with acetic anhydride being especially preferred. The amount of alkanoylating agent used should be 1–4, preferably 2–3, molar equivalents, with the reaction with the 1-(4-methoxybenzyl)-3,4,5,6,7,8-hexahydro-isoquinoline of formula III above then proceeding as quantitatively as possible.

As weak organic bases which are inert under the reaction conditions and which are suitable for the purpose of the present invention there come into consideration tert. amines, preferably dialkylanilines, for example, dimethylaniline or diethylaniline, pyridine, picolines, for example, α-picoline, quinoline, isoquinoline and the like. The use of dimethylaniline is especially preferred.

For the lower-alkanoylation reaction step, the reaction solution from the Bischler-Napieralski cyclization is optionally diluted with an aprotic organic solvent which is inert under the reaction conditions. Suitable solvents for this purpose are especially ethers, such as methyl t-butyl ether, tetrahydrofuran and dioxan, aromatic hydrocarbons, such as toluene, nitrites, such as acetonitrile or propionitrile, and the like. Preferably, dilution is carried out with the same solvent in which the Bischler-Napieralski cyclization has been carried out. The use of toluene is also especially preferred here.

The following Example for the production of (Z)-1-[1-(4-methoxybenzylidene)-1,2,3,4,5,6,7,8-octahydro-isoquinolin-2-yl]ethanone by the cyclization of N-(2-cyclohex-1-enylethyl)-2-(4-methoxyphenyl)acetamide and subsequent N-alkanoylation illustrates an especially advantageous embodiment of the process in accordance with the invention, but it does not in any manner represent a limitation. All temperatures are given in degrees Celsius.

EXAMPLE 27.34 g (100 mmol) of N-(2-cyclohex-1-enylethyl)-2-(4-methoxyphenyl)acetamide in 30 ml of toluene were placed in a 350 ml four-necked flask fitted with a magnetic stirrer, thermometer, gas outlet having a paraffin oil seal and a motorized piston burette. The oxygen dissolved therein was removed by evacuating the reaction suspension while stirring to boiling and thereafter releasing the vacuum by the addition of argon (this procedure is referred to hereinafter as inertization). 4.73 ml (51 mmol) of distilled phosphorus oxychloride were dosed in while stirring at 80° within 60 minutes. The solution was left to react at 80° for 1 hour, thereafter at 90° for 2 hours and finally at 100° for a further 1 hour. The reaction mixture was thereafter treated with 90 ml of inertized toluene and then treated with 20.7 ml (220 mmol) of inertized acetic anhydride. Then, 19.01 ml (150 mmol) of N,N-dimethylaniline, distilled under an inert gas, were added. The reaction mixture was stirred, firstly at 70° for 18 hours and thereafter at room temperature for 24 hours. After cooling to about 10°, 50 ml of ice-cold water were added. After stirring for 10 minutes, the toluene phase was separated and the aqueous phase was extracted with 2×100 ml of toluene. The 3 toluene phases were washed with 3×25 ml of 1N ice-cold hydrochloric acid and 2×25 ml of water. The toluene phases were subsequently washed with 1×50 ml of 2 molar, ice-cold sodium hydroxide solution and 2×25 ml of water, combined and concentrated in a water-jet vacuum to 52.2 g (the solution contained crude (Z)-1-[1-(4-methoxybenzylidene)-1,2,3,4,5,6,7,8-octahydro-isoquinolin-2-yl]ethanone as well as toluene).

The above 52.2 g of residue and 2.6 g of a second crystallizate of (Z)-1-[1-(4-methoxybenzylidene)-1,2,3,4,5,6,7,8-octahydro-isoquinolin-2-yl]ethanone from a previous batch were placed under an inert gas atmosphere in a 250 ml three-necked round flask fitted with a reflux condenser, thermometer and paddle stirrer. The suspension was dissolved by heating to 60°. Then, 27.5 g of n-hexane were added thereto and the solution was thereafter seeded at 50° with (Z)-1-[1-(4-methoxybenzylidene)-1,2,3,4,5,6,7,8-octahydro-isoquinolin-2-yl]ethanone. The suspension obtained was then cooled to 0° in a water bath while stirring. After 18 hours at 0°, the mixture was suction filtered and the residue was rinsed with 10 ml of an ice-cold 4:6 mixture of toluene and n-hexane. The crystallizate was dried to constant weight at 45° in a water-jet vacuum, with 26.1 g of a first crystallizate of (Z)-1-[1-(4-methoxybenzylidene)-1,2,3,4,5,6,7,8-octahydro-isoquinolin-2-yl]ethanone of melting point 103°–4° being obtained, yield 87%, content=99% (according to HPLC).

The filtrate from the first crystallization was evaporated in a water-jet vacuum, with 5.5 g of a residue being obtained. This anhydrous residue was dissolved in 10 ml of toluene and the solution was inertized. 1 ml of a 1 molar solution of acetyl chloride in toluene and 0.5 ml of a 1 molar solution of acetic acid in toluene were added to this solution. The thus-obtained solution was stirred under an inert gas atmosphere, firstly at about 40° for 6 hours and thereafter at room temperature for about 18 hours. Then, a solution of 12 ml of a 0.75 molar sodium hydroxide solution in 50% aqueous methanol was added at room temperature in one portion. After stirring the reaction mixture at room temperature for 10 minutes, the two-phase mixture was extracted with 2×20 ml of toluene. The organic phases were washed with 2×20 ml of water, 2×20 ml of 0.1N hydrochloric acid and 2×20 ml of water, combined and subsequently evaporated in a water-jet vacuum. The residue was crystallized from 20 g of diisopropyl ether. After leaving to stand at 0° for 18 hours, the crystallizate was filtered off under suction and rinsed with 5 ml of ice-cold diisopropyl ether. The filter cake was dried at 45° in a water-jet vacuum for 4 hours, there being obtained 3.2 g of a second crystallizate of (Z)-1-[1-(4-methoxybenzylidene)-1,2,3,4,5,6,7,8-octahydro-isoquinolin-2-yl]-ethanone.

I claim:

1. A process for the production of (Z)-1-[1-(4-methoxybenzylidene)-1,2,3,4,5,6,7,8-octahydro-isoquinolin-2-yl]alkanones of the formula

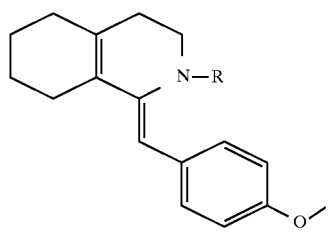

wherein R is lower alkanoyl,
which process comprises cyclizing by a Bischler-Napieralski reaction N-(2-cyclohex-1-enylethyl)-2-(4-methoxyphenyl)acetamide of the formula

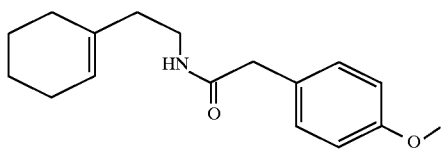

to produce 1-(4-methoxybenzyl)-3,4,5,6,7,8-hexahydro-isoquinoline of the formula

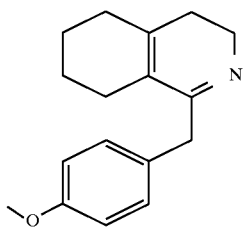

under an inert gas atmosphere, and further comprising carrying out the Bischler-Napieralski reaction in the presence of 0.45 to 0.8, molar equivalents of phosphorus oxychloride; and lower-alkanoylating the resulting 1-(4-methoxybenzyl)-3,4,5,6,7,8-hexahydro-isoquinoline in situ, in the presence of a weak organic base which is inert under the reaction conditions.

2. A process according to claim 1, wherein the phosphorous oxychloride is present in an amount of from 0.5 to 0.55 molar equivalents.

3. A process according to claim 1, wherein the Bischler-Napieralski reaction is carried out in an aprotic solvent selected from the group consisting of toluene, xylene, propionitrile and butyronitrile, and at a temperature between about 70° C. and a temperature just below the reflux temperature of the reaction mixture.

4. A process according to claim 3, wherein the aprotic solvent is toluene or propionitrile and the reaction temperature is between about 80° C. and 110° C.

5. A process according to claim 4, wherein the aprotic solvent is toluene and the reaction temperature is between about 80° C. and 100° C.

6. A process according to claim 1, wherein the weak organic base is a tert-amine.

7. A process according to claim 6, wherein the weak organic base is a dialkylaniline, pyridine, a picoline, quinoline or isoquinoline.

8. A process according to claim 7, wherein the weak organic base is dimethylaniline.

9. A process according to claim 1, wherein the reaction solution from the Bischler-Napieralski reaction is diluted with an aprotic organic solvent which is inert under the reaction conditions.

10. A process according to claim 9, wherein the aprotic organic solvent is the same solvent in which the Bischler- Napieralski reaction has been carried out and is an ether, an aromatic hydrocarbon, or a nitrile.

11. A process according to claim 10, wherein the aprotic organic solvent is selected from methyl t-butyl ether, tetrahydrofuran, dioxan, toluene, acetonitrile or propionitrile.

12. A process according to claim 1, wherein the weak organic base is present in an amount of 2–4 molar equivalents based on phosphorus oxychloride.

13. A process according to claim 1, further comprising using oxygen-free solvents and reagents in the lower-alkanoylation reaction.

14. A process according to claim 1, wherein the lower-alkanoylation reaction is carried out at a temperature between about room temperature and 80° C. and wherein the alkanoylating agent is present in an amount of 1–4 molar equivalents based on phosphorus oxychloride.

15. A process according to claim 14, wherein the alkanoylating agent is present in an amount of 2–3 molar equivalents based on phosphorus oxychloride.

16. A process according to claim 14, wherein the alkanoylating agent is acetic anhydride.

* * * * *